United States Patent

Polski

[11] Patent Number: 5,128,187
[45] Date of Patent: Jul. 7, 1992

[54] ATTACHMENT TAPE FOR FOAM-BACKED ABSORBENT PRODUCT

[75] Inventor: Stephen P. Polski, St. Paul, Minn.

[73] Assignee: Minnesota Mining and Manufacturing Company, St. Paul, Minn.

[21] Appl. No.: 625,956

[22] Filed: Dec. 11, 1990

[51] Int. Cl.$^5$ .............................................. A61F 13/02
[52] U.S. Cl. ................................. 428/40; 428/317.1; 428/317.3; 428/317.7; 428/354; 428/355; 604/385.1; 604/387; 604/389
[58] Field of Search ................... 428/40, 317.1, 317.3, 428/354, 317.7, 355; 604/387, 389, 385.1; 427/208

[56] References Cited

U.S. PATENT DOCUMENTS

| | | | |
|---|---|---|---|
| 3,239,478 | 3/1966 | Harlan, Jr. | 260/27 |
| 3,932,328 | 1/1976 | Korpman | 260/27 |
| 3,954,692 | 5/1976 | Downey | 260/33.6 |
| 3,959,189 | 5/1976 | Kitamori | 260/2.5 B |
| 4,096,203 | 6/1978 | St. Clair | 260/876 B |
| 4,136,699 | 1/1979 | Collins | 604/387 |
| 4,203,815 | 5/1980 | Noda et al. | 204/159.2 |
| 4,213,925 | 7/1980 | Kiyono et al. | 264/22 |
| 4,252,906 | 2/1981 | Hosokawa et al. | 521/86 |
| 4,358,489 | 11/1982 | Green | 428/317.3 |
| 4,554,191 | 11/1985 | Korpman | 428/35 |
| 4,681,577 | 7/1987 | Stern | 604/389 |
| 4,850,991 | 7/1989 | Nakanishi | 428/317.7 |
| 5,019,072 | 5/1991 | Polski | 604/389 |
| 5,028,646 | 7/1991 | Miller | 604/389 |

FOREIGN PATENT DOCUMENTS 139484 9/1984 United Kingdom .

Primary Examiner—Ellis P. Robinson
Assistant Examiner—Nasser Ahmad
Attorney, Agent, or Firm—Gary L. Griswold; Roger R. Tamte; William J. Bond

[57] ABSTRACT

A polyethylene-containing foam-backed absorbent article having an adhesive patch comprised of 25 to 50 parts of an A-B block copolymer and 25-50 parts of solid tackifying resin and liquid resin and/or plasticizing oil. The adhesive not exhibiting any adhesive transfer when removed from a cotton fabric after one hour at 100° F. and 0.25 P.S.I.

14 Claims, 1 Drawing Sheet

ATTACHMENT TAPE FOR FOAM-BACKED ABSORBENT PRODUCT

BACKGROUND AND FIELD OF THE INVENTION

This invention relates to an improved pressure-sensitive adhesive transfer tape for use with polyethylene foam-backed absorbent products for attachment to cotton, or like, undergarments. The polyethylene foam backing is a flexible liquid-impermeable shell partially surrounding an absorbent core material.

Sanitary absorbent articles, such as sanitary napkins, conventionally comprise a liquid-impermeable backing covering at least one side of an absorbent core with a liquid-permeable facing on the side facing the fluid discharge source.

Sanitary absorbent articles such as urinary pads have been proposed in EP139,484 which use backings, flexible shells, of thermoformed polyethylene-containing polymer foam. This foam backing yields a soft, conformable article designed to withstand ordinary stress and strains and maintain a relatively large liquid storage capacity. Absorbent articles of this type are adhered to the clothing of the user conventionally with adhesive patches. These patches are placed on the liquid-impermeable backings of the absorbent articles. With absorbent articles using polyethylene-containing foam backings or shells the adhesive patches would be located on the outer face of the foam.

Placing adhesive on polyethylene-containing foam presents significant problems. Such foam has low bonding abilities to conventional adhesives. Further polyethylene containing foams are heat sensitive making hot melt coating of adhesives onto the foam an impractical option. These problems are addressed in U.S. Pat No. 4,554,191, which proposes using a double faced tape on a backing having a non-recoverable extensibility of less than 100%. The two faces of the tape are designed to have differential adhesive levels (preferably at least 1.4 to 1). The side provided with the stronger adhesive level is attached to the polyethylene-containing foam. The side with the lower level of adhesion is used to attach the absorbent article to the user's undergarment. This differential adhesion level is asserted to prevent transfer of adhesive to the undergarment or delamination of the foam. Differential levels of adhesion is allegedly accomplished using different adhesive formulations on either side of the tape backing or by masking or likewise lowering the exposed adhesive surface area on the lower adhesive level face of the tape backing. The use of the specified non-extensible backing is also stressed as critical to get acceptable performance (e.g., lack of adhesive transfer). The adhesive taught and exemplified is a A-B block copolymer elastomer tackified with solid tackifying resins. More resin is stated as needed to get the higher adhesion level formulation. The A-B block copolymer specifically described is an admixture of A-B diblock and A-B-A triblock (polystyrene-polyisoprene-polystyrene).

The problem with the U.S. Pat No. 4,554,191 approach is that the tape and its application is extremely complicated and the tape is difficult to manufacture. Conventional transfer coating tapes (a single unsupported layer of adhesive on a release surface) would be preferable in terms of simplicity. However, transfer tape methods for applying an adhesive patch are characterized as unacceptable by U.S. Pat. No. 4,554,191 for polyethylene-containing foam substrates. Transfer-applied adhesive has no backing and no inherent differential adhesion levels.

SUMMARY OF THE INVENTION

It has been found that certain adhesive formulations can be provided as an unsupported (no backing) adhesive patch on a release liner, which can be adhered to polyethylene-containing foam without adhesive transfer or foam delamination when used to attach the foam backed absorbent article to conventional undergarments.

In brief summary, the adhesive composition comprises:
(a) 25 to 50 weight percent of an A-B elastomeric block copolymer with the A blocks preferably comprised of styrene and preferably comprising 10 to 30% of the copolymer and the B block comprising a polymer derived from a conjugated diene. Preferable the B block is derived from isoprene or butadiene;
(b) 50 to 75 weight percent of a solid tackifying resin preferably with a liquid tackifier and/or plasticizing oil where the adhesive when laminated to a polyethylene containing foam backing does not exhibit adhesive transfer to fabric when removed (as defined herein) therefrom after one hour at 100° F. (37.8° C.) and 0.25 PSI (17.6 gm/cm$^2$) pressure.

DETAILED DESCRIPTION OF THE PREFERRED EMBODIMENTS

Figure 2:
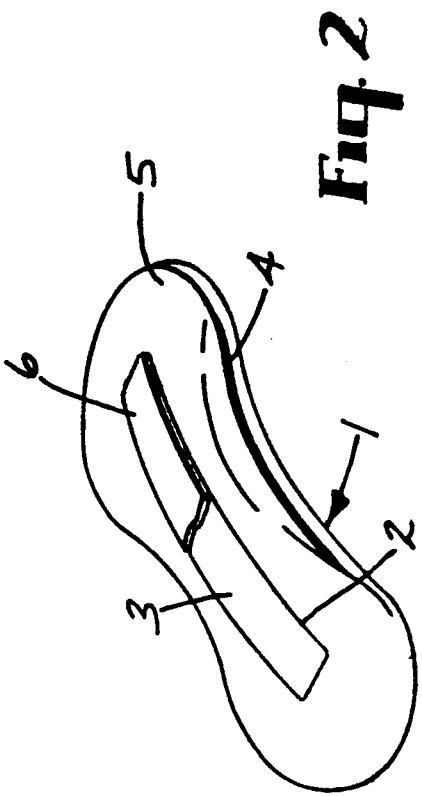
FIG. 2 is a bottom perspective view of an absorbent article in accordance with the disclosed invention.

The absorbent article of the invention is such as is depicted in FIG. 2. The absorbent product shown is a urinary pad 1. The pad 1 comprises a thermoformed shell 5 of a polyethylene-containing foam. The foam shell is formed into a fluid retaining shape with upstanding side edges 4. The foam shell is impermeable to moisture so as to hold liquid while preventing leakage onto the user's garments. The top (not shown) surface of the foam shell is open to allow entry of fluids into the shell (preferably through a liquid-permeable facing sheet) which contains the absorbent core material (not shown).

The shell is provided with an adhesive attachment patch 2 on the outer surface of the shell 5. The adhesive attachment patch 2 comprises a layer of pressure-sensitive adhesive 3 as is described herein, and a release-coated substrate 6. The adhesive 3 is preferably applied by transfer application of the adhesive onto the foam shell from the release substrate 6. The release substrate remains in contact with the adhesive until removed by the end user to expose the adhesive attachment patch 2.

The adhesive layer 3 comprises an A-B block copolymer, preferably an A-B-A linear, radial or star triblock or diblock copolymer, as described, for example in U.S. Pat No. 3,239,478, and 4,096,203. The A block is a monoalkenyl arene, preferably styrene, having a molecular weight between 2,000 and 125,000, preferably between 7,000 and 30,000. The A block content is from about 10 to 50 percent, more preferably between 10 and 30 percent. Other suitable A blocks include alphamethyl styrene, t-butyl styrene and other ring alkylated styrenes as well as mixtures thereof. B is an elastomeric conjugated diene, having an average molecular weight of from about 5,000 to about 1,000,000, preferably between about 15,000 to about 300,000 and more preferably from 50,000 to 180,000. The B block is preferably an isoprene or butadiene, with isoprene being most preferred. Although preferably A-B-A and A-B triblock and diblock copolymers will comprise the majority of the elastomer of the adhesive other conventional diene elastomers may be used to a minor extent, i.e., up to 25 percent of the elastomer, such as natural rubber; butadiene, isoprene or butadiene-styrene rubber; butadiene-acrylonitrile; butyl rubber or block copolymers of these diene elastomers. The preferred elastomeric block copolymers are used in an amount ranging from about 33 to 50 weight percent, preferably at least about 38 weight percent of the adhesive composition.

The tackifying resin component generally comprises a blend of a solid tackifying resin and a liquid tackifying resin, a single solid or liquid tackifying resin, or a blend of solid tackifying resin and liquid plasticizer and/or liquid tackifying resin. The tackifying resins can be selected from the group of resins at least partially compatible with the B blocks of the preferred elastomeric block copolymer materials of this invention. Such tackifying resins include those aliphatic hydrocarbon resins made from the polymerization of a feed stream consisting mainly of unsaturated species containing four to six carbon atoms; rosin esters and rosin acids (particularly with butadiene containing A-B-A block copolymers); mixed aliphatic/aromatic tackifying resins; polyterpene tackifiers; and hydrogenated tackifying resins. The hydrogenated resins can include resins made from the polymerization and subsequent hydrogenation of a feedstock consisting mostly of dicyclopentadiene; resins produced from the polymerization and subsequent hydrogenation of pure aromatic feedstocks such as styrene, alphamethylstyrene, vinyl toluene; resins fashioned from the polymerization and subsequent hydrogenation of an unsaturated aromatic feedstream wherein the feedstream mainly contains species having from 7 to 10 carbon atoms; hydrogenated polyterpene resins; and hydrogenated aliphatic and aliphatic/aromatic resins. Preferred tackifying resins include the aliphatic hydrocarbon resins (particularly for isoprene and butadiene B block copolymers) and the hydrogenated resins (particularly for ethylene-butylene B block copolymers). Especially preferred are the aliphatic hydrocarbon resins.

The liquid plasticizers suitable for use in the adhesive compositions of this invention include naphthenic oils, paraffinic oils, aromatic oils and mineral oils. Preferred plasticizing liquids include naphthenic oils and slightly aromatic oils.

The adhesive preferably is tackified with a solid tackifying resin with a liquid plasticizer or liquid resin of the above described preferred types with a weight ratio of liquid to solid of from 0 to about 0.7, preferably from 0 to 0.4 and most preferably from 0 to 0.3.

A preferred solid tackifying resin is one that is compatible with the elastomeric conjugated diene block and has a softening point between 80° C. and 115° C., such as is produced from polymerization of a stream of aliphatic petroleum derivatives of dienes and monoolefins having 4 to 9 carbon atoms as is disclosed in U.S. Pat. Nos. 3,932,328 and 3,954,692. Particularly preferred with isoprene mid-block elastomers are tackifying resins resulting from the copolymerization of a feed comprised predominately of $C_5$ carbon atom species such as piperylene, 2-methyl-2-butene or isoprene, commercially available, for example, as Wingtack TM 95 and Wingtack TM Plus, respectively, available from Goodyear Chemical Co., Akron, Ohio.

The adhesive compositions can also be modified with well known additives such as pigments, fillers, stabilizers and antioxidants for their conventional purposes.

Transfer tape versions of the adhesive are formed by placing the adhesive described above on a conventional release substrate. The substrate can suitably be formed of a synthetic polymer such as polyolefins (e.g., polypropylene), polyesters, polyamides or the like. Natural backings such as Kraft paper backings may also be used. The transfer adhesive can be applied by any conventional method including melt coating, gravure, coextrusion, solvent coating and the like.

The adhesive on the transfer tape can then be transferred to the polyethylene foam substrate by conventional techniques.

The polyethylene-containing foams are produced in accordance with the teachings of U.S. Pat. Nos. 4,213,925, 4,203,815, 3,959,189 and 4,252,906 and are commercially available under the trademark "Volara" from Voltek, Inc., Lawrence, Massachusetts. This foam can be readily formed into the desired shape by conventional techniques such as thermal molding at about 260° F. (127° C.). The particular shape of the shell is not critical and depends on the particular use contemplated for the absorbent article. The thicknesses for the foam can be as is described in U.S. Pat No. 4,554,191 and EP0139484, namely from about 1/64 to ¼ inch (0.4 to 6 mm). The preferred foam material is formed from an ethylene/vinyl acetate copolymer which is crosslinked.

The release substrate 6 is coated with conventional release agents such as a silicone treatment. This coating is at least on the face of the substrate in contact with the adhesive layer 3 when it is on the foam shell 5. Preferably, a silicone or like release agent is provided on both sides of the release substrate 6 allowing the transfer adhesive to be wound into a roll form. However, in this case, the backside release agent should have a lower level of adhesion to the adhesive so that the adhesive does not transfer to the backside of the release substrate. Alternatively, a separate release-coated substrate can be provided, which also would have a release coating with a higher level of release than the release substrate 6 face contacting the adhesive. This separate release-coated substrate would then be removed prior to placement of the transfer tape on the foam shell.

The following examples are the currently contemplated preferred modes for carrying out the invention and should not be considered as limiting thereof unless otherwise indicated.

EXAMPLES 1-26

Adhesives were formulated using a blend of a styrene-isoprene-styrene block copolymer (Kraton TM 1107, available from Shell Chemical Co., Beaupre, Ohio) a solid $C_5$ aliphatic hydrocarbon tackifying resin (Wingtack TM Plus) and a naphthenic oil (Shellflex TM 371, available from Shell Chemical Co., Beaupre, Ohio). The formulations and their performance characteristics are summarized in Table 1. The adhesives were coated onto a silicone treated paper using a knife coater at 8.0 grains/24 in$^2$ (34 gm/m$^2$) from a solution of 50% solids in toluene. The solvent was removed by placing the samples in a forced air oven at 150° F. for 5 minutes.

The solution-coated release tapes (transfer tapes) were then tested for adhesive transfer or foam delamination. The examples were tested by first forming a laminate of the transfer tape with a polyethylene containing foam (Volara TM 4A) using a 4.5 pound roller, two passes. One by five inch samples were then cut from the laminate and the release film was removed. A two by eight inch piece of cotton (woven with 36 threads per inch in each direction) was then placed onto the exposed adhesive face of the laminate and rolled down, from the foam side, with a 250 gram roller (two passes). The three-layer laminate (foam/adhesive/cotton) was then placed between two Kiel plates, which generated a pressure of 0.25 P.S.I., for one hour at 100° F. The samples were then allowed to come to room temperature for 15 minutes. At this time the cotton was separated from the adhesive coated foam by holding the foam and cotton and pulling them apart at 180° (T-peel). Any adhesive picking (any visible adhesive remaining on the cotton) was considered a transfer of adhesive to the cotton as a minimum standard. Any more severe adhesive transfer, with or without delamination of the foam, was similarly indicated in Table 1 as a case of adhesive transfer without further comment. The formulations of these examples were made using a preferred composition and exhibited acceptable performance in regions a-c of FIG. 1.

The shear values for examples 1-11 were tested using a shear stand adjusted to a negative 5 degree angle. A two inch wide double-coated tape was used to attach the cotton to the shear stand. The one end of a sample of foam with the example adhesive was then attached to the cotton with a 200 gram weight on the opposing end. All examples indicated a shear value of 1000 minutes or more. See attached test method.

TABLE I

| Ex. | Rubber | % Rubber | Oil/Resin Adhesive Ratio | Transfer | Shear (Minutes) |
|---|---|---|---|---|---|
| 1 | K-1107 | 42.5 | 0.08 | no | 1000+ |
| 2 | K-1107 | 35.0 | 0.16 | no | 1000+ |
| 3 | K-1107 | 35.0 | 0 | no | 1000+ |
| 4 | K-1107 | 35.0 | 0 | no | 1000+ |
| 5 | K-1107 | 50.0 | 0 | no | 1000+ |
| 6 | K-1107 | 42.5 | 0.08 | no | 1000+ |
| 7 | K-1107 | 35.0 | 0.16 | no | 1000+ |
| 8 | K-1107 | 50.0 | 0 | no | 1000+ |
| 9 | K-1107 | 50.0 | 0.16 | no | 1000+ |
| 10 | K-1107 | 50.0 | 0.16 | no | 1000+ |
| 11 | K-1107 | 42.5 | 0.08 | no | 1000+ |
| 12 | K-1107 | 35.0 | 0.16 | no | |
| 13 | K-1107 | 35.0 | 0.3 | no | |
| 14 | K-1107 | 30.0 | 0.3 | no | |
| 15 | K-1107 | 25.0 | 0.3 | no | |
| 16 | K-1107 | 35.0 | 0.4 | no | |
| 17 | K-1107 | 30.0 | 0.4 | no | |
| 18 | K-1107 | 25.0 | 0.4 | no | |
| 19 | K-1107 | 20.0 | 0.4 | yes | |
| 20 | K-1107 | 35.0 | 0.6 | no | |
| 21 | K-1107 | 30.0 | 0.6 | no | |
| 22 | K-1107 | 25.0 | 0.6 | yes | |
| 23 | K-1107 | 20.0 | 0.6 | yes | |
| 24 | K-1107 | 30.0 | 0.16 | no | |
| 25 | K 1107 | 25.0 | 0.3 | no | |
| 26 | K-1107 | 35.0 | 0.4 | no | |

EXAMPLES 27-34

This series of examples was based on a formulation comprising a styrene-ethylene/butylene-styrene block copolymer, (Kraton TM 1657), a solid hydrogenated dicyclopentadien C9 resin (Escorez TM 5380, available from Exxon Chemical Co., Houston, Texas) and a naphthenic oil (Shellflex TM 371). The examples were formed and tested as per Examples 1-26 above. The results are set forth in Table II below. This system was a less preferred system and gave acceptable results only in region a of FIG. 1.

TABLE II

| Ex. | Rubber | % Rubber | Oil/Resin Adhesive Ratio | Transfer | Shear (Minutes) |
|---|---|---|---|---|---|
| 27 | K-1657 | 30.0 | 0.16 | no | |
| 28 | K-1657 | 30.0 | 0.3 | no | |
| 29 | K-1657 | 25.0 | 0.3 | no | |
| 30 | K-1657 | 20.0 | 0.3 | yes | |
| 31 | K-1657 | 30.0 | 0.4 | yes | |
| 32 | K-1657 | 25.0 | 0.4 | yes | |
| 33 | K-1657 | 20.0 | 0.4 | yes | |
| 34 | K-1657 | 25.0 | 0.6 | yes | 15 |

EXAMPLES 35-38

These examples used the identical adhesive formulation of Examples 1-26 with the exception of using a liquid C5 aliphatic hydrocarbon resin (Wingtack TM 10) instead of a naphthenic oil. The summary of the testing results and the formulations tested are set forth in Table III below.

Figure 1:
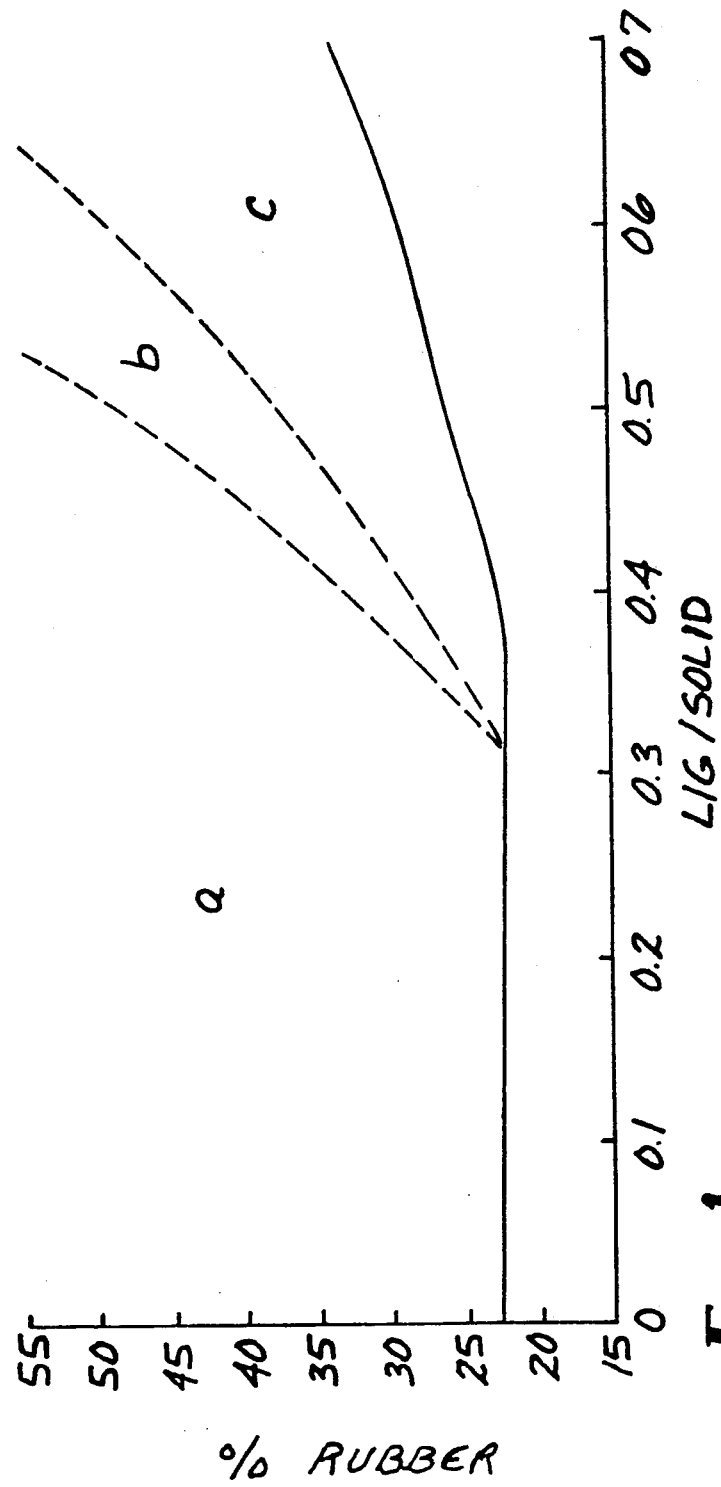
FIG. 1 is a diagram showing the preferred compositional space for various adhesive systems exemplified.

Acceptable performance for this system was noted in regions a and b of FIG. 1.

TABLE III

| Ex. | Rubber | % Rubber | Oil/Resin Adhesive Ratio | Transfer |
|---|---|---|---|---|
| 35 | K-1107 | 20.0 | 0.3 | yes |
| 36 | K-1107 | 25.0 | 0.4 | yes |
| 37 | K-1107 | 30.0 | 0.4 | no |
| 38 | K-1107 | 25.0 | 0.3 | no |

EXAMPLES 39-42

These examples used adhesive formulations comprised of a styrene-butadiene-styrene block copolymer (Kraton TM 1101), a naphthenic oil (Shellflex TM 371) and a resin ester solid resin (Floral TM 85 available from Hercules Chem Co., Wilmington, Del.).

The samples were prepared and tested as per examples 35-38 above. The results and formulations are set forth in Table IV below. Acceptable results for this system were noted in regions a-c of FIG. 1.

TABLE IV

| Ex. | Rubber | % Rubber | Oil/Resin Adhesive Ratio | Transfer |
|---|---|---|---|---|
| 39 | K-1101 | 20.0 | 0.3 | yes |
| 40 | K-1101 | 25.0 | 0.4 | no |
| 41 | K-1101 | 30.0 | 0.4 | no |
| 42 | K-1101 | 25.0 | 0.3 | no |

Other embodiments of the invention will be apparent to those skilled in the art from the consideration of the specification or practice of the invention disclosed herein. It is intended that the specifications and examples be considered as exemplary, with the true scope and spirit of the invention being indicated by the following claims.

I claim:

1. A sanitary absorbent article adapted to attach to a garment comprising a polyethylene-containing foam liquid-impermeable backing having an outer face and an inner face, an absorbent core adjacent said inner face and an unsupported transfer patch, said transfer patch comprising pressure-sensitive adhesive on said outer face, said pressure-sensitive adhesive about 25 to 50 weight percent of an A-B elastomeric block copolymer with the A block comprised of styrene and comprising 10 to 30 percent of the copolymer and the B block comprising a polymer derived from a conjugated diene, and b) about 50 to 75 weight percent of a solid tackifying resin, or solid tackifying resin and liquid tackifying resin and/or plasticizer oil wherein the adhesive when contacted to an undergarment or the like at 250 grams of pressure does not transfer from or delaminate the foam after one hour at 100° F. and 0.25 P.S.I.

2. The absorbent article of claim 1 wherein the B block is derived from isoprene or butadiene and the tackifier is a mixture of liquid tackifier resin and/or liquid plasticizer and solid tackifier resin in a ratio of from 0 to about 0.7.

3. The absorbent article of claim 2 wherein the tackifier is an admixture of solid tackifying resin and a naphthenic oil.

4. The absorbent article of claim 1 wherein the B block is an ethylene-butylene copolymer and the tackifier is a mixture of hydrogenated solid resin and liquid resin or plasticizing oil with a ratio of liquid to solid of from 0 to about 0.5.

5. The absorbent article of claim 1 wherein the polyethylene containing foam is a crosslinked ethylene/vinylacetate copolymer with a thickness of from about 1/64 to about ¼ inch.

6. The absorbent article of claim 1 wherein the backing has upstanding sides surrounding said absorbent core with a liquid-permeable facing sheet covering the top of said absorbent core and adhered to the sides of said backing.

7. The absorbent article of claim 1 wherein the transfer patch comprises a transfer tape portion with said pressure-sensitive adhesive on a substrate coated with a release agent on at least the face in contact with the adhesive layer.

8. The absorbent article of claim 1 wherein the undergarment comprises a cotton attachment region.

9. The absorbent article of claim 4 wherein the solid or liquid resins are compatible with the B blocks.

10. The absorbent article of claim 2 wherein the solid or liquid resins are compatible with the B blocks.

11. The absorbent article of claim 2 wherein the resins are aliphatic hydrocarbon resins.

12. The absorbent article of claim 3 wherein the resins are aliphatic hydrocarbon resins.

13. The absorbent article of claim 12 wherein the liquid-to-solid ratio is from 0.0 to 0.4.

14. The absorbent article of claim 12 wherein the liquid-to-solid ratio is from 0.0 to 0.3.

* * * * *

UNITED STATES PATENT AND TRADEMARK OFFICE
CERTIFICATE OF CORRECTION

PATENT NO. : 5,128,187
DATED : July 7, 1992
INVENTOR(S) : Stephen P. Polski

It is certified that error appears in the above-identified patent and that said Letters Patent is hereby corrected as shown below:

Column 4, line 22, delete "U.$." and insert --U.S.--.

Column 6, line 1, delete "dicyclopentadien" and insert --dicyclopentadiene--.

Column 7, line 5, after the word "adhesive" and before the word "about" insert --consisting essentially of a) --.

Signed and Sealed this

Tenth Day of August, 1993

Attest:

MICHAEL K. KIRK

Attesting Officer    Acting Commissioner of Patents and Trademarks